(12) United States Patent
Yin et al.

(10) Patent No.: US 8,653,121 B2
(45) Date of Patent: Feb. 18, 2014

(54) AGROCHEMICAL COMPOSITION AND METHOD FOR PREPARING AND USING THE SAME

(75) Inventors: Amanda Yin, Kunshan (CN); Sonia Chen, Jiangsu (CN); Yifan Wu, Kunshan (CN); Pichumani Narayanamoorthy, Kunshan (CN); Chang Yuan Lo, Kunshan (CN)

(73) Assignee: Rotam Agrochem International Co., Ltd., Hong Kong (CN)

(*) Notice: Subject to any disclaimer, the term of this patent is extended or adjusted under 35 U.S.C. 154(b) by 391 days.

(21) Appl. No.: 12/602,066

(22) PCT Filed: May 28, 2008

(86) PCT No.: PCT/CN2008/071116
§ 371 (c)(1),
(2), (4) Date: Sep. 14, 2010

(87) PCT Pub. No.: WO2008/145063
PCT Pub. Date: Dec. 4, 2008

(65) Prior Publication Data
US 2012/0071530 A1    Mar. 22, 2012

(30) Foreign Application Priority Data
May 28, 2007    (CN) .......................... 2007 1 0022965

(51) Int. Cl.
*A01N 43/653*    (2006.01)
*A01P 3/00*    (2006.01)
*C07D 249/08*    (2006.01)

(52) U.S. Cl.
USPC ...................................... 514/383; 548/262.2

(58) Field of Classification Search
USPC ...................................... 514/383; 548/262.2
See application file for complete search history.

(56) References Cited

U.S. PATENT DOCUMENTS

| 3,342,673 A | 9/1967 | Kaufman et al. |
| 5,206,225 A | 4/1993 | Hortsmann et al. |
| 5,225,570 A | 7/1993 | Williams et al. |
| 5,256,630 A | 10/1993 | Bussler |

FOREIGN PATENT DOCUMENTS

| DE | 4341986 A1 | 6/1995 |
| UA | 41866 C2 | 10/2001 |
| WO | 95/15685 A1 | 6/1995 |
| WO | WO-2005104844 A1 | 11/2005 |
| WO | WO-2008145063 A1 | 12/2008 |

OTHER PUBLICATIONS

First Office Action received from Russian Patent Office regarding Application No. 2009146754/20 (066630), dated Dec. 17, 2009. Summary/Partial Translation of the Office Action provided by Unitalen Attorneys at Law.
Extended European Search Report regarding Application No. 08757529.6-2103, dated Apr. 6, 2011.
Russian Decision on Grant regarding Application No. 2009146754, dated Jan. 25, 2013.

*Primary Examiner* — Sreeni Padmanabhan
*Assistant Examiner* — Jason A Deck
(74) *Attorney, Agent, or Firm* — Harness, Dickey & Pierce, P.L.C.

(57) ABSTRACT

An agrochemical composition comprises an azole active ingredient and an N,N-dialkyl long chain alkylamide. The N,N-dialkyl long chain alkylamide is present in sufficient amount to prevent or inhibit the crystallization of the azole derivative during the application of the composition to a locus. Preferred N,N-Dialkyl long chain alkylamide(s) comprised in the composition is/are selected from the group consisting of compounds of the formula (I): in which (a) $R^1$ and $R^2$ are independently normal alkyl radicals having 2 carbon atoms, and R represents an alkyl group having from 10 to 30 carbon atoms; or (b) $R^1$ and $R^2$ are independently normal alkyl radicals having 3 carbon atoms, and R represents an alkyl group having from 9 to 30 carbon atoms; or 20 (c) $R^1$ and $R^2$ are independently normal alkyl radicals having from 4 to 20 carbon atoms and R represents an alkyl group having from 6 to 30 carbon atoms. The composition is particularly advantageous when formulated with a fungicide, in particular one or more of tebuconazole, cyproconazole, difenoconazole, diniconazole, triticonazole, hexaconazole, triflumiazole, metconazole, tricyclazole, flusilazole, flutriafol, and myclobutanil.

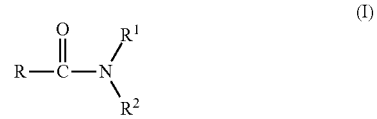

27 Claims, No Drawings

AGROCHEMICAL COMPOSITION AND METHOD FOR PREPARING AND USING THE SAME

CROSS-REFERENCE TO RELATED APPLICATIONS

This application is a 371 U.S. National Stage of International Application No. PCT/CN2008/071116, filed May 28, 2008. This application claims the benefit of Chinese Patent Application No. 200710022965.0, filed May 28, 2007. The disclosures of the above applications are incorporated herein by reference.

FIELD OF THE INVENTION

The present invention relates to an agrochemical composition. The invention is especially concerned with such compositions comprising one or more compounds active as a fungicide. The present invention further relates to a method of preparing the aforementioned compositions and their use in crop protection. The present invention is particularly concerned with the inhibition of crystal growth in aqueous spray liquors based on azole pesticidal compounds and to compositions exhibiting reduced crystal growth.

BACKGROUND OF THE INVENTION

Perhaps the most prevalent practice for applying pesticides to plants is by spraying aqueous liquors onto the plants to be treated. The spray equipment customarily used for the application of aqueous formulations of plant treatment agents is well known in the art and generally comprises one or more filters and/or nozzles. Some technical difficulties are associated with spraying practice when predominantly aqueous compositions of pesticides which are essentially water insoluble, are employed. In such cases, often the filters and nozzles are clogged as a result of crystal growth of the water insoluble active ingredients. Certain pesticidally active azole derivates show a particular tendency to crystallize in such situations.

A particular method for overcoming this problem is by inhibiting or preventing the crystal growth of the pesticide in the sprayer parts by employing a crystal growth inhibitor in the pesticidal composition. Thus, U.S. Pat. No. 5,206,225 describes the use of certain alkyl carboxylic acid dimethylamides as crystallization inhibitors of azole fungicides. Further, U.S. Pat. No. 5,369,118 describes the use of alkyl lactam as a crystal growth inhibitor of azole fungicides.

The crystal growth inhibitors disclosed in the prior publications do not offer a solution for all needs, practices and conditions employed in agriculture. Thus, there is an ongoing need to develop further crystal growth inhibitors applied in agriculture which overcome the shortcoming of the prior art and to provide formulations comprising such inhibitors.

DETAILED DESCRIPTION OF THE INVENTION

In the present invention it is surprisingly found that certain N,N-dialkyl long chain alkylamides are useful for preventing the crystallization during the application of aqueous spray liquors having azole derivatives as the active agrochemical ingredient.

U.S. Pat. No. 5,206,225 discloses the use of varieties of alkylcarboxylic acid dimethylamide of the formula R—CO—N(CH$_3$)$_2$ as crystallization inhibitors of azole fungicides. Although U.S. Pat. No. 5,206,225 describes the R group may represent alkyl having 5 to 19 carbon atoms, the amide group is exclusively dimethylamide. Thus, U.S. Pat. No. 5,206,225 teaches away from developing other dialkylamide derivatives for using as a crystallization inhibitor in agrochemical composition comprising azole derivatives as active ingredients.

DE 4,341,986 is concerned with the use of carboxylic acid amides having the general formula R—CO—N(R$_1$R$_2$) as crystallization inhibitors, in particular for fungicidally active compounds. DE 4,341,986 discloses a very wide range of compounds having the aforementioned formula and suggests that compounds of the aforementioned formula in which R is hydrogen, alkyl having from 1 to 16 carbon atoms, hydroxy alkyl having from 1 to 10 carbon atoms, alkenyl having from 2 to 16 carbon atoms, cycloalkyl having from 5 to 7 carbon atoms, cycloalkyl having from 5 to 7 carbon atoms, aralkyl having from 6 to 10 carbon atoms in the aryl group and from 1 to 4 carbon atoms in the alkyl chain, aralkenyl having from 6 to 10 carbon atoms in the alkyl group and from 2 to 4 carbon atoms in the alkenyl chain, phenoxyalkyl having from 1 to 4 carbon atoms in the alkyl or a wide range of amide groups, and in which R$^1$ is hydrogen, alkyl having from 1 to 12 carbon atoms, hydroxyalkyl having from 1 to 8 carbon atoms, alkenyl having from 2 to 12 carbon atoms, optionally substituted cycloalkyl having from 5 to 7 carbon atoms, phenyl, benzyl or phenethyl, and R$^2$ is alkyl having from 2 to 12 carbon atoms, hydroxyalkyl having from 1 to 8 carbon atoms, alkenyl having from 2 to 12 carbon atoms, optionally substituted cycloalkyl having from 5 to 7 carbon atoms, phenyl, benzyl or phenethyl may inhibit the crystallization of a wide range of azole derivatives.

DE 4,341,986 indicates a very large number of carboxylic acid amides and prefers to have R, R$_1$ and R$_2$ different classes of groups, in particular mixing saturated groups, such as alkyl and cycloalkyl, with unsaturated group, such as alkenyl, phenyl-containing groups, and amide groups. DE 4,341,986 discloses within the very broad range of carboxylic acid amides indicated a range of alkyl amides. However, DE 4,341,986 favours the use of carboxylic acid amides in which lower alkyl groups are present, that is in which the length of the alkyl chain and/or the total number of alkyl carbon atoms is low. In particular, of the alkyl amides specifically exemplified in table 2 of DE 4,341,986, representing a minority of the carboxylic amides exemplified in table 2 of 986', R is an alkyl group having 11 carbon atoms or fewer, with an emphasis being placed on R being a lower alkyl group. Further, of the alkyl amides specifically exemplified, the total number of carbon atoms in the alkyl groups of R, R$_1$ and R$_2$ does not exceed 16.

In the present invention, the surprising finding is that alkyl amides of the general formula of DE 4,341,986 in which R is a higher alkyl group, in particular, depending upon the nature of R$_1$ and R$_2$ in the formula having at least 6 carbon atoms, and/or the total number of carbon atoms in the alkyl groups of R, R$_1$ and R$_2$ exceeds 16, exhibit a markedly superior activity to inhibiting crystallization of a specific class of azole derivatives.

Based on the above surprising finding, the present invention relates to a use of certain N,N-dialkyl long chain alkylamides for preventing the crystallization during the application of aqueous spray liquors having azole derivatives as the active agrochemical ingredient. It has been found that such N,N-Dialkyl long chain alkylamides are particularly effective as crystal growth inhibitor in spray liquors comprising azole derivatives as active ingredients.

Accordingly, in a first aspect, the present invention provides an agrochemical composition comprising an azole active ingredient and a N,N-dialkyl long chain alkylamide.

More particularly, in the first aspect, the present invention provides an agrochemical composition comprising an N,N-dialkyl long chain alkylamide of the formula (I)

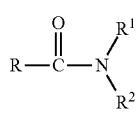

in which:

(a) $R^1$ and $R^2$ are independently normal alkyl radicals having 2 carbon atoms, and R represents an alkyl group having from 10 to 30 carbon atoms; or (b) $R^1$ and $R^2$ are independently normal alkyl radicals having 3 carbon atoms, and R represents an alkyl group having from 9 to 30 carbon atoms; or (c) $R^1$ and $R^2$ are independently normal alkyl radicals having from 4 to 20 carbon atoms and R represents an alkyl group having from 6 to 30 carbon atoms;

and at least one azole active ingredient having the general formula (II)

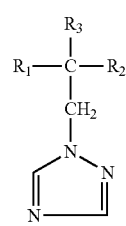

in which $R_1$ represents phenyl, 4-chlorophenyl, 4-chlorophenylethyl, 4-fluorophenyl, 2,4-dicholorophenyl, or 4-chlorophenyloxy;

$R_2$ represents n-butyl, tert-butyl, phenyl, 2-fluorophenyl or a group of the general formula (III):

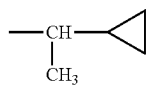

and $R_3$ represents hydroxyl, oxygen or cyano, and optionally at least one member selected from the group consisting of a surface-active agent, organic diluent and low temperature stabilizer.

The azole active ingredients are water insoluble compounds and such compounds are prone to crystallizing in aqueous compositions. However, the compositions are generally applied in the form of an aqueous liquor, prepared by the dilution of a concentrate with water. The N,N-dialkyl long chain alkylamide is present in the composition in an amount sufficient to reduce and/or inhibit crystal growth formation of the azole active ingredient. It has been found that the N,N-dialkyl long chain alkylamides are effective in reducing and/or inhibiting crystal growth of azole active compounds. Thus, the inclusion of one or more N,N-dialkyl long chain alkylamides in the aqueous composition prevents the spray equipment and the like from being blocked and makes the spray liquor free of any crystals. This in turn maintains the composition in a more homogeneous condition. In addition, it has been found that the use of the N,N-dialkyl long chain alkylamides to prevent crystal formation and growth improves the efficiency and efficacy of the active ingredient.

The N,N-dialkyl long chain alkylamides are present in an amount sufficient to reduce and/or inhibit crystal growth of the azole compounds. The amount of the N,N-dialkyl long chain alkylamide present may depend upon the concentration of the azole active ingredient and may be determined by routine experimentation. The N,N-dialkyl long chain alkylamides are preferably present in an amount such as to give a weight ratio of the azole active ingredient to the N,N-dialkyl long chain alkylamide of from 1:0.1 to 1:5, more preferably from 1:1 to 1:4.

The composition may comprise a single N,N-dialkyl long chain alkylamide or a combination of two or more N,N-dialkyl long chain alkylamides.

The N,N-Dialkyl long chain alkylamide(s) comprised in the composition of the present invention is/are selected from the group consisting of compounds of the formula I:

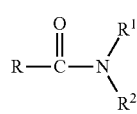

in which, (a) $R^1$ and $R^2$ are normal alkyl radicals having 2 carbon atoms, and R represents an alkyl group having 10 to 30 carbon atoms, more preferably from 11 to 18 carbon atoms;

(b) $R^1$ and $R^2$ are normal alkyl radicals having 3 carbon atoms, then R represents an alkyl group having 9 to 30 carbon atoms, more preferably from 9 to 18 carbon atoms; and (c) $R^1$ and $R^2$ are normal alkyl radicals having 4 to 20 carbon atoms, more preferably from 4 to 8 carbon atoms, R represents an alkyl group having 6 to 30 carbon atoms, more preferably from 6 to 18 carbon atoms.

Alkyl groups present as R in the compounds of formula (I) may be straight chain or branched.

In one embodiment of the present invention, it is preferred that the alkyl groups R, $R^1$ and $R^2$ contain, in total, greater than 16 carbon atoms, more preferably greater than 18 carbon atoms, especially greater than 20 carbon atoms.

According to a preferred embodiment of the present invention, the preferred N,N-dialkyl long chain alkylamides are selected from the group consisting of diethyldodecanamide, diethyltridecanamide, N,N-diethyltetradecanamide, N,N-diethylhexadecanamide, N,N-diethylheptadecanamide, N,N-diethyloctadecanamide, N,N-diethylnonadecanamide, N,N-dipropyldecanamide, N,N-dipropyldodecanamide, N,N-dipropyltridecanamide, N,N-dipropyltetradecanamide, N,N-diethylhexadecanamide, N,N-dipropylheptadecanamide, N,N-dipropyl octadecanamide, N,N-dipropylnonadecanamide, N,N-dibutylheptamide, N,N-dibutyloctanamide, N,N-dibutylnonamide, N,N-dibutyldecanamide, N,N-dibutyldodecanamide, N,N-dibutyltridecanamide, N,N-dibutyltetradecanamide, N,N-dibutylhexadecanamide, N,N-dibutylheptadecanamide, N,N-dibutyloctadecanamide, N,N-dibutylnonadecanamide, N,N-dipentyloctanamide, N,N-dipentyldecanamide, N,N-dipentyldodecanamide, N,N-dipentyltetradecanamide, N,N-dipentylhexadecanamide, N,N-dipentyloctadecanamide, or any mixture thereof.

The composition of the present invention may be a concentrate, which is diluted with water prior to application on the plants to be treated. In this case, the one or more N,N-dialkyl long chain alkylamides are preferably present in an amount of from 5% to 80% by weight, more preferably from 20% to 60% by weight.

As noted above, it has been found that N,N-dialkyl long chain alkylamides are effective in reducing or inhibiting the crystal formation of certain azole derivatives active as agrochemicals, in particular pesticides. The composition may comprise one or more azole derivative active ingredients.

The N,N-dialkyl long chain alkylamides are particularly effective in preventing the crystallization of azole derivatives that are active as fungicides. In particular, the N,N-dialkyl long chain alkylamides have been found to be effective as inhibiting crystal growth in aqueous formulations of azole derivatives of the general formula (II):

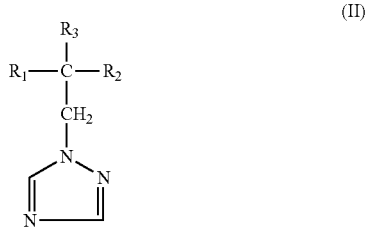

(II)

in which $R_1$ represents phenyl, 4-chlorophenyl, 4-chlorophenylethyl, 4-fluorophenyl, 2,4-dicholorophenyl, or 4-chlorophenyloxy;

$R_2$ represents n-butyl, tert-butyl, phenyl, 2-fluorophenyl or a group of the general formula (III):

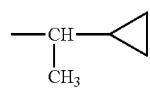

(III)

and $R_3$ represents hydroxyl, oxygen or cyano.

Preferred compounds of the general formula (II) are those in which $R_1$ represents 4-chlorophenyl. Compounds of the general formula (II) in which $R_2$ represents tert-butyl are also preferred. In addition, compounds in which $R_3$ is a hydroxyl group are also preferred.

A particularly preferred compound for use in the composition of the present invention is tebuconazole, which is the compound of general formula (II) in which $R_1$ is 4-chlorophenyl, $R_2$ is tert-butyl and $R_3$ is hydroxyl. The concentrate of the present invention has been found to be particularly stable when used to formulate tebuconazole, without any reduction in the fungicidal activity of the compound when applied to a locus. Tebuconazole is a well known compound in the art and is available commercially.

A further preferred compound for use in the composition of the present invention is hexaconazole, which is the compound of general formula (II) in which $R_1$ is 2,4-dichlorophenyl, $R_2$ is n-butyl and $R_3$ is hydroxyl. The concentrate of the present invention has been found to be particularly stable when used to formulate hexaconazole, without any reduction in the fungicidal activity of the compound when applied to a locus. Again, hexaconazole is a well known compound in the art and is available commercially.

A further preferred compound for use in the composition of the present invention is cyproconazole, that is the compound of general formula (II) in which $R_1$ is 4-chlorophenyl, $R_2$ is a group of general formula (III) and $R_3$ is hydroxyl. The concentrate of the present invention has been found to be particularly stable when used to formulate cyproconazole, without any reduction in the fungicidal activity of the compound when applied to a locus. Cyproconazole is a well known compound in the art and is available commercially.

A further preferred compound for use in the composition of the present invention is myclobutanil, that is the compound of general formula (II) in which $R_1$ is 4-chlorophenyl, $R_2$ is n-butyl and $R_3$ is cyano. The concentrate of the present invention has been found to be particularly stable when used to formulate myclobutanil, without any reduction in the fungicidal activity of the compound when applied to a locus. Myclobutanil is a well known compound in the art and is available commercially.

A further preferred compound for use in the composition of the present invention is flutriafol, that is the compound of general formula (II) in which $R_1$ is 4-fluorophenyl, $R_2$ is 2-fluorophenyl and $R_3$ is hydroxyl. The concentrate of the present invention has been found to be particularly stable when used to formulate flutriafol, without any reduction in the fungicidal activity of the compound when applied to a locus. Flutriafol is a well known compound in the art and is available commercially.

The compositions of the present invention have also been found to be effective in preventing the crystallization of triadimefon, that is a compound of general formula (II) in which $R^1$ is 4-chlorophenyloxy, $R^2$ is tert-butyl and $R^3$ is oxygen. Triadimefon is a commercially available fungicide.

In other embodiments, the composition of the present invention comprises one or more of difenoconazole, diniconazole, propiconazole, tricyclazole, triticonazole, triflumizole, flusilazole, metconazole.

In one embodiment, the formulation contains azole derivatives as active ingredients selected from the group consisting of tebuconazole, cyproconazole, difenoconazole, diniconazole, triticonazole, hexaconazole, triflumiazole, metconazole, tricylazole, flusilazole, flutriafol, myclobutanil and mixtures thereof.

The composition to be applied to the plants to be treated, in particular by spraying, may contain the active azole derivative in any suitable concentration. As noted above, the spray liquors are typically prepared by the dilution with water of a concentrate. Typically, the spray liquor contains azole active ingredients from 0.0001 to 3%, more preferably 0.002 to 2%, by weight.

In addition to one or more N,N-dialkyl long chain alkylamides and one or more azole derivative active ingredients, the compositions of the present invention may comprise other components, including one or more of organic diluents or solvents, water and emulsifiers. Suitable components are known in the art.

Organic diluents or solvents that may be included in the composition include both polar and non-polar organic solvents, for example ketones, amides, such as dimethyl formamide, and aromatic hydrocarbons, such as xylene. Other suitable solvents will be known to the person skilled in the art.

Suitable emulsifiers comprised in the compositions of the present invention are also known in the art and commercially available. Suitable emulsifiers include both ionic and non-ionic emulsifiers, such as fatty acid esters, fatty alcohol esters, ethers, alkyl sulphonates and aryl sulphonates. Other suitable surface active components will also be known to the person skilled in the art.

Further components comprised in the composition are well known in the art and include, for example stabilizers and thickeners. Such components are commercially available and their use will be recognized and understood by the person skilled in the art.

In a further aspect, the present invention provides an aqueous spray composition comprising an azole active ingredient and an N,N-dialkyl long chain alkylamide, as hereinbefore defined, and water.

Other components that may be included in the aqueous spray composition are as hereinbefore described. Details of the components of the aqueous spray composition are as given hereinbefore.

In a further aspect, the present invention provides the use of N,N-dialkyl long chain alkylamides, in particular the N,N-dialkyl long chain alkylamides as hereinbefore defined, to inhibit the crystal growth of pesticidally active azole derivatives.

The compositions of the present invention may be prepared using techniques known in the art. A particularly preferred method of preparing the composition is as follows:

Each component is added according to the weight fraction required in the final composition. First, the solvent, and one or more N,N-dialkyl long chain alkylamide crystallization inhibitors are charged to a suitable mixing vessel, for example a blending tank equipped with a hot water circulation. The resulting mixture is agitated. The one or more azole derivatives are added to the mixture and the agitation continued until all azole derivatives are dissolved completely in the solvent. An agitation time of about 30 minutes is typical. Thereafter, further components, such as emulsifiers, if present, are added and the mixture further agitated to ensure homogeneity. A further agitation time of about 1 hour is typical.

When the composition is to be sprayed, the formulation is diluted with water to the desired concentration of active ingredient, for example by adding the concentrated formulation to water in a vessel with stirring.

In a further aspect, the present invention comprises a method of preventing crystallization of pesticidal liquid formulations comprising azole derivatives during application, the method comprising adding a N,N-dialkyl long chain alkylamide as hereinbefore defined to the formulation in an amount sufficient to reduce crystallization of the azole derivative.

In still a further aspect, the present invention provides a method of treating pests at a locus comprising applying to the locus a composition as hereinbefore described. The composition is preferably applied in the form of a diluted aqueous formulation. The method is particularly suitable for the application of fungicides to treat fungal infestations of plants in the locus.

Embodiments of the present invention will now be described, by way of example only.

EXAMPLES

In each of the following examples, a composition was prepared according to the following general methodology:

Charge every component based on the recipe composition into a vessel in the following manner. First, add the solvent and crystallization inhibitor to a blending tank equipped with a hot water circulation; agitate the solution; add one or more azole active ingredients into the blending tank; continue agitating for 30 minutes until all azole active ingredients are dissolved completely; add the emulsifiers to the tank; continue agitating for one hour until the mixture is uniform; stop agitating.

Samples of each composition prepared were taken from the tank and analysed in accordance with the international testing methods CIPAC (Collaborative International Pesticides Analytical Council).

To test the crystallization properties, in each case 20 L of an aqueous spray liquor, prepared by dilution of the composition prepared with water to a concentrate content of 0.5% by weight, were pumped in circulation through a fine-meshed sieve for 1 hour in a flow-through apparatus with the aid of a pump. The solution after preparation was analyzed in a chromatograph to measure the concentration of the azole derivative active ingredient in PPM. The gauge pressure of the liquid being circulated was recorded every one hour. An increase in the pressure is an indication the nozzles and the fine-meshed sieve are being blocked by crystals. Every hour, a sample of the circulating liquid was taken and analyzed in the chromatograph to determine the concentration of the azole derivative active ingredient.

The preparation and the crystallization behavior of various spray liquors according to the present invention, prepared and tested as described above, are described in the following examples, taken in conjunction with comparative test results given in the respective table.

Example 1

The liquid formulation described in Table 1 was prepared containing N,N-dialkyl long chain alkylamides, wherein the weight ratio of tebuconazole and N,N-dialkyl long chain alkylamides was approx 1:1.8. Crystal formation of this formulation was compared with a second liquid formulation, which was prepared from identical components in an identical manner, but without any crystallization inhibitors.

The formulation of Example 1 contained N,N-dialkyl long chain alkylamides in an amount of 45% wt. Table 1 describes the liquid formulation of Example 1 and the comparison formulation, Comparison A.

TABLE 1

| EXAMPLE 1: Tebuconazole EC (with Crystallization inhibitors) | | COMPARISON A: Tebuconazole EC (without Crystallization inhibitors) | | |
|---|---|---|---|---|
| Component | Composition | Component | Composition | Remark |
| Tebuconazole tech | 250 kg (as pure) | Tebuconazole tech | 250 kg (as pure) | Active ingredient |
| Calcium dodecylphenyl-sulfonate | 100 kg | Calcium dodecylphenyl-sulfonate | 100 kg | Emulsifier |
| TWEEN 80 Sorbitan monooleate ethoxylate | 100 kg | TWEEN 80 Sorbitan monooleate ethoxylate | 100 kg | Emulsifier |
| Cyclohexanone | 100 kg | Cyclohexanone | 550 kg | Solvent |
| N,N-diethyl dodecanamide | 450 kg | | | Crystallization inhibitor |
| Total | 1000 kg | Total | 1000 kg | |

Use Example I

The experimental results are set forth in the following table.

| | Example I | | | Comparison A | | |
|---|---|---|---|---|---|---|
| | Press. (PSI) 200 mesh | Tebuconazole (ppm) | Tebuconazole decrease % | Press. (PSI) 200 mesh | Tebuconazole (ppm) | Tebuconazole decrease % |
| Initial solution | 40 | 1059 | 0 | 38 | 1141 | 0 |
| After 1 h | 40 | 1043 | −1.51 | Nozzles 100% blocked | | |
| After 2 h | 40 | 1028 | −2.93 | Nozzles 100% blocked | | |
| After 3 h | 41 | 1002 | −5.38 | | | |
| After 4 h | 41 | 988 | −6.70 | | | |

Example 2

The liquid formulation was prepared containing N,N-dialkyl long chain alkylamides, wherein the weight ratio of diniconazole and N,N-dialkyl long chain alkylamides was approx 1:5. Crystal formation of this formulation was compared with a second liquid formulation, which was prepared from identical components in an identical manner, but without any crystallization inhibitors.

The formulation of Example 2 contained N,N-dialkyl long chain alkylamides in an amount of 80% wt. Table 2 describes the liquid formulation of Example 2 and the comparison formulation, Comparison B.

TABLE 2

| EXAMPLE 2: Diniconazole EC (with Crystallization inhibitors) | | COMPARISON B: Diniconazole EC (without Crystallization inhibitors) | | |
|---|---|---|---|---|
| Component | Composition | Component | Composition | Remark |
| Diniconazole tech | 160 kg (as pure) | Diniconazole tech | 160 kg (as pure) | Active ingredient |
| Rhodocal 70 | 10 kg | Rhodocal 70 | 10 kg | Emulsifier |
| Calcium dodecylphenyl-sulphonate | | Calcium dodecylphenyl-sulphonate | | |
| Tween 80 Sorbitan monooleate ethoxylate | 10 kg | Tween 80 Sorbitan monooleate ethoxylate | 10 kg | Emulsifier |
| N-methyl pyrrolidone | 20 kg | N-methyl pyrrolidone | 820 kg | Solvent |
| N,N-diethylnona-decanamide | 800 kg | | | Crystallization inhibitors |
| Total | 1000 kg | Total | 1000 kg | |

Use Example II

The experimental results are set forth in the following table.

|  | Example 2 | | | Comparison B | | |
| --- | --- | --- | --- | --- | --- | --- |
|  | Pressure (PSI) 200 mesh | Diniconazole (ppm) | Diniconazole decrease % | Pressure (PSI) 200 mesh | Diniconazole (ppm) | Diniconazole decrease % |
| Initial solution | 39 | 755 | 0 | 38 | 780 | 0 |
| After 1 h | 39 | 746 | −1.19 | 40 | 532 | −31.75 |
| After 2 h | 39 | 732 | −3.05 | 42 | 440 | −43.70 |
| After 3 h | 40 | 728 | −3.58 | 46 | 369 | −52.74 |
| After 4 h | 40 | 699 | −7.42 | 49 | 335 | −57.12 |

Example 3

The liquid formulation was prepared containing N,N-dialkyl long chain alkylamides, wherein the weight ratio of difenconazole and N,N-dialkyl long chain alkylamides was approx 1:3.33. Crystal formation of this formulation was compared with a second liquid formulation, which was prepared from identical components in an identical manner, but without any crystallization inhibitors.

The formulation of Example 3 contained N,N-dialkyl long chain alkylamides in an amount of 50% wt. Table 3 describes the liquid formulation of Example 3 and the comparison formulation, Comparison C.

TABLE 3

| EXAMPLE 3: Difenoconazole EC (with Crystallization inhibitors) | | COMPARISON C: Difenoconazole EC (without Crystallization inhibitors) | | |
| --- | --- | --- | --- | --- |
| Component | Composition | Component | Composition | Remark |
| Difenoconazole tech | 150 kg (as pure) | Difenoconazole tech | 150 kg (as pure) | Active ingredient |
| Rhodocal 70 Sodium dodecylphenyl-sulphonate | 100 kg | Rhodocal 70 Sodium dodecylphenyl-sulphonate | 100 kg | Emulsifier |
| IGEPAL BC/9 Nonylphenol ethoxylate | 100 kg | IGEPAL BC/9 Nonylphenol ethoxylate | 100 kg | Emulsifier |
| Dimethyl formamide | 150 kg | Dimethyl formamide | 650 kg | Solvent |
| N,N-dipropyl-decanamide | 200 kg |  |  | Crystallization inhibitor |
| N,N-diethyl-dodecanamide | 300 kg |  |  | Crystallization inhibitor |
| Total | 1000 kg | Total | 1000 kg |  |

Use Example III

The experimental results are set forth in the following table.

|  | Example 3 | | | Comparison C | | |
| --- | --- | --- | --- | --- | --- | --- |
|  | Press. (PSI) 200 mesh | Difenoconazole (ppm) | Difenoconazole decrease % | Press. (PSI) 200 mesh | Difenoconazole (ppm) | Difenoconazole decrease % |
| Initial solution | 40 | 660 | 0 | 38 | 664 | 0 |
| After 1 h | 40 | 655 | −0.70 | 40 | 459 | −30.97 |
| After 2 h | 40 | 647 | −1.84 | 42 | 373 | −43.81 |
| After 3 h | 40 | 643 | −2.54 | 44 | 313 | −52.82 |
| After 4 h | 41 | 611 | −7.44 | 44 | 282 | −57.55 |

Example 4

The formulation of Example 4 was prepared with a combination of tebuconazole and triadimefon. The liquid formulation was prepared containing N,N-dialkyl long chain alkylamides, wherein the weight ratio of tebuconazole and triadimefon to N,N-dialkyl long chain alkylamides was approximately 1:0.1. Crystal formation of this formulation was compared with a second liquid formulation, which was prepared from identical components in an identical manner, but without any crystallization inhibitors.

The formulation of Example 4 contained N,N-dialkyl long chain alkylamides in an amount of 5% wt. Table 4 describes the liquid formulation of Example 4 and the comparison formulation, Comparison D.

TABLE 4

| EXAMPLE 4: Tebuconazole•Triadimefon EC (Containing Crystallization inhibitor) | | COMPARISON D: Tebuconazole•Triadimefon EC (Not containing Crystallization inhibitor) | | |
|---|---|---|---|---|
| Component | Composition | Component | Composition | Remark |
| Tebuconazole tech | 100 kg (as pure) | Tebuconazole tech | 100 kg (as pure) | Active ingredient |
| Triadimefon tech | 400 kg (as pure) | Triadimefon tech | 400 kg (as pure) | Active ingredient |
| Rhodocal 70 Calcium dodecylphenyl sulphonate | 100 kg | Rhodocal 70 Calcium dodecylphenyl sulphonate | 100 kg | Emulsifier |
| Emulsogen EL 540 Castor oil ethoxylate | 100 kg | Emulsogen EL 540 Castor oil ethoxylate | 100 kg | Emulsifier |
| Dimethyl formamide | 250 kg | Dimethyl formamide | 300 kg | Solvent |
| N,N-dipropyl-nonadecan-amide | 25 kg | | | Crystallization inhibitor |
| N,N-dipropyl-decanamide | 25 kg | | | Crystallization inhibitor |
| Total | 1000 kg | Total | 1000 kg | |

Use Example IV

The experimental results are set forth in the following table.

Example 5

The liquid formulation was prepared containing N,N-dialkyl long chain alkylamides, wherein the weight ratio of propiconazole and N,N-dialkyl long chain alkylamides was approx 1:2. Crystal formation of this formulation was compared with a second liquid formulation, which was prepared from identical components in an identical manner, but without any crystallization inhibitors.

The formulation of Example 5 contained N,N-dialkyl long chain alkylamides in an amount of 40% wt. Table 5 describes the liquid formulation of Example 5 and the comparison formulation, Comparison E.

TABLE 5

| EXAMPLE 5: Propiconazole EC (Containing Crystallization inhibitor) | | COMPARISON E: Propiconazole EC (Not Containing Crystallization inhibitor) | | |
|---|---|---|---|---|
| Component | Composition | Component | composition | Remark |
| Propiconazole tech | 200 kg (as pure) | Propiconazole tech | 200 kg (as pure) | Active ingredient |
| Agnique ABS 70 C | 100 kg | Agnique ABS 70 C | 100 kg | Emulsifier |
| Calcium dodecylphenyl sulphonate | | Calcium dodecylphenyl sulphonate | | |
| Emulsogen EL 540 Castor oil ethoxylate | 100 kg | Emulsogen EL 540 Castor oil ethoxylate | 100 kg | Emulsifier |
| Dimethyl formamide | 200 kg | Dimethyl formamide | 600 kg | Solvent |
| N,N-diethyl dodecanamide | 300 kg | | | Crystallization inhibitor |
| N,N-dibutyl-heptamide | 100 kg | | | Crystallization inhibitor |
| Total | 1000 kg | Total | 1000 kg | |

| | Example 4 | | | | | Comparison D | | | | |
|---|---|---|---|---|---|---|---|---|---|---|
| | Press. (PSI) 200 mesh | Tebuconazole (TB) (ppm) | Triadimefon (TRI) (ppm) | TB decrease % | TRI Decrease % | Press. (PSI) 200 mesh | Tebuconazole (TB) (ppm) | Triadimefon (TRI) (ppm) | TB decrease % | TRI decrease % |
| Initial Solution | 40 | 448 | 1765 | 0 | 0 | 38 | 445 | 1760 | 0 | 0 |
| After 1 h | 40 | 432 | 1756 | −3.57 | −0.51 | Nozzles 100% blocked | | | | |
| After 2 h | 40 | 426 | 1743 | −4.91 | −1.25 | Nozzles 100% blocked | | | | |
| After 3 h | 41 | 410 | 1735 | −8.48 | −1.70 | | | | | |
| After 4 h | 42 | 402 | 1720 | −10.26 | −2.55 | | | | | |

Use Example V

The experimental results are set forth in the following table.

|  | Example 5 | | | Comparison E | | |
|---|---|---|---|---|---|---|
|  | Pressure (PSI) 200 mesh | Propiconazole (ppm) | Propiconazole decrease % | Pressure (PSI) 200 mesh | Propiconazole (ppm) | Propiconazole decrease % |
| Initial solution | 39 | 878 | 0 | 38 | 884 | 0 |
| After 1 h | 39 | 862 | −1.82 | 40 | 624 | −29.41 |
| After 2 h | 39 | 850 | −3.19 | Nozzles 100% blocked | | |
| After 3 h | 40 | 838 | −4.56 | Nozzles 100% blocked | | |
| After 4 h | 40 | 820 | −6.61 | | | |

Example 6

The formulation of Example 6 was prepared with a combination of hexaconazole and myclobutanil as active ingredients. The liquid formulation was prepared containing N,N-dialkyl long chain alkylamides, wherein the weight ratio of hexaconazole and myclobutanil to N,N-dialkyl long chain alkylamides was approx 1:1.8. Crystal formation of this formulation was compared with a second liquid formulation, which was prepared from identical components in an identical manner, but without any crystallization inhibitors.

The formulation of Example 6 contained N,N-dialkyl long chain alkylamides in an amount of 45% wt. Table 6 describes the liquid formulation of Example 6 and the comparison formulation, Comparison F.

TABLE 6

| EXAMPLE 6: Hexaconazole•Myclobutanil EC (Containing Crystallization inhibitor) | | COMPARISON F: Hexaconazole•Myclobutanil EC (without Crystallization inhibitor) | | |
|---|---|---|---|---|
| Component | Composition | Component | Composition | Remark |
| Hexaconazole tech | 100 kg (as pure) | Hexaconazole tech | 100 kg (as pure) | Active ingredient |
| Myclobutanil tech | 150 kg (as pure) | Myclobutanil tech | 150 kg (as pure) | Active ingredient |
| Agnique ABS 70 C | 100 kg | Agnique ABS 70 C | 100 kg | Emulsifier |
| Calcium dodecylphenyl sulphonate | | Calcium dodecylphenyl sulphonate | | |
| Alkamuls OR/36 | 100 kg | Alkamuls OR/36 | 100 kg | Emulsifier |
| Castor oil ethoxylate | | Castor oil ethoxylate | | |
| Dimethyl formamide | 100 kg | Dimethyl formamide | 550 kg | Solvent |
| N,N-diethyl dodecanamide | 450 kg | | | Crystallization inhibitor |
| Total | 1000 kg | Total | 1000 kg | |

Use Example VI

The experimental results are set forth in the following table.

|  | Example 6 | | | | | Comparison F | | | | |
|---|---|---|---|---|---|---|---|---|---|---|
|  | Press. (PSI) 200 mesh | Hexaconazole (HEX) (ppm) | Myclobutanil (MYC) (ppm) | HEX decrease % | MYC decrease % | Press. (PSI) 200 mesh | Hexaconazole (HEX) (ppm) | Myclobutanil (MYC) (ppm) | HEX decrease % | MYC Decrease % |
| Initial solution | 40 | 450 | 657 | 0 | 0 | 38 | 445 | 664 | 0 | 0 |
| After 1 h | 40 | 438 | 648 | 2.67 | −1.37 | Nozzles 100% blocked | | | | |
| After 2 h | 40 | 430 | 633 | 4.44 | −3.65 | Nozzles 100% blocked | | | | |
| After 3 h | 41 | 422 | 625 | 6.22 | −4.88 | | | | | |
| After 4 h | 42 | 408 | 614 | 9.33 | −6.55 | | | | | |

Example 7

The formulation of Example 7 was prepared containing N,N-dialkyl long chain alkylamides, wherein the weight ratio of tebuconazole to N,N-dialkyl long chain alkylamides was approx 1:1. Crystal formation of this formulation was compared with a second liquid formulation, which was prepared from identical components in an identical manner, but without any crystallization inhibitors.

The formulation of Example 7 contained N,N-dialkyl long chain alkylamides in an amount of 30% wt. Table 7 describes the liquid formulation of Example 7 and the comparison formulation, Comparison G.

TABLE 7

| EXAMPLE 7: Tebuconazole EC (with Crystallization inhibitor) | | COMPARISON G: Tebuconazole EC (without Crystallization inhibitor) | | |
|---|---|---|---|---|
| Component | Composition | Component | Composition | Remark |
| Tebuconazole tech | 300 kg (as pure) | Tebuconazole tech | 300 kg (as pure) | Active ingredient |
| Agnique ABS 70 C Calcium dodecylphenyl sulphonate | 100 kg | Agnique ABS 70 C Calcium dodecylphenyl sulphonate | 100 kg | Emulsifier |
| Alkamuls OR/36 Castor oil ethoxylate | 100 kg | Alkamuls OR/36 Castor oil ethoxylate | 100 kg | Emulsifier |
| Butanole | 200 kg | Butanole | 500 kg | Solvent |
| N,N-dibutyl-nona-decanamide | 150 kg | | | Crystallization inhibitor |
| N,N-dibutyl-decanamide | 150 kg | | | Crystallization inhibitor |
| Total | 1000 kg | Total | 1000 kg | |

Use Example VII

The experimental results are set forth in the following table.

| | Example 7 | | | Comparison G | | |
|---|---|---|---|---|---|---|
| | Pressure (PSI) 200 mesh | Tebuconazole (ppm) | Tebuconazole decrease % | Pressure (PSI) 200 mesh | Tebuconazole (ppm) | Tebuconazole decrease % |
| Initial solution | 40 | 1400 | 0 | 38 | 1398 | 0 |
| After 1 h | 40 | 1380 | −1.43 | 39 | 685 | −51.0 |
| After 2 h | 40 | 1300 | −7.14 | Nozzles 100% blocked | | |
| After 3 h | 40 | 1280 | −8.57 | Nozzles 100% blocked | | |
| After 4 h | 42 | 1200 | −14.3 | | | |

Example 8

The formulation of Example 8 was prepared containing N,N-dialkyl long chain alkylamides, wherein the weight ratio of Myclobutanil to N,N-dialkyl long chain alkylamides was approx 1:0.5. Crystal formation of this formulation was compared with a second liquid formulation, which was prepared from identical components in an identical manner, but without any crystallization inhibitors.

The formulation of Example 8 contained N,N-dialkyl long chain alkylamides in an amount of 20% wt. Table 8 describes the liquid formulation of Example 8 and the comparison formulation, Comparison H.

TABLE 8

| EXAMPLE 8: Myclobutanil EC (with Crystallization inhibitors) | | COMPARISON H: Myclobutanil EC (without Crystallization inhibitors) | | |
|---|---|---|---|---|
| Component | Composition | Component | Composition | Remark |
| Myclobutanil tech | 400 kg (as pure) | Myclobutanil tech | 400 kg (as pure) | Active ingredient |
| Agnique ABS 60C Calcium dodecylphenyl sulphonate | 100 kg | Agnique ABS 60C Calcium dodecylphenyl sulphonate | 100 kg | Emulsifier |
| Alkamuls OR/36 Castor oil ethoxylate | 100 kg | Alkamuls OR/36 Castor oil ethoxylate | 100 kg | Emulsifier |
| Methanol | 200 kg | Methanol | 400 kg | Solvent |
| N,N-dipentyl-octanamide | 100 kg | | | Crystallization inhibitor |
| N,N-diethyl-dodecanamide | 100 kg | | | Crystallization inhibitor |
| Total | 1000 kg | Total | 1000 kg | |

Use Example VIII

The experimental results are set forth in the following table.

|  | Example 8 | | | Comparison H | | |
| --- | --- | --- | --- | --- | --- | --- |
|  | Pressure (PSI) 200 mesh | Myclobutanil (ppm) | Myclobutanil decrease % | Pressure (PSI) 200 mesh | Myclobutanil (ppm) | Myclobutanil decrease % |
| Initial solution | 40 | 1700 | 0 | 38 | 1660 | 0 |
| After 1 h | 40 | 1657 | −2.53 | Nozzles 100% blocked | | |
| After 2 h | 40 | 1605 | −5.59 | Nozzles 100% blocked | | |
| After 3 h | 40 | 1574 | −7.41 | | | |
| After 4 h | 42 | 1526 | −10.23 | | | |

Example 9

The formulation of Example 9 was prepared containing N,N-dialkyl long chain alkylamides, wherein the weight ratio of diniconazole to N,N-dialkyl long chain alkylamides was approx 1:3. Crystal formation of this formulation was compared with a second liquid formulation, which was prepared from identical components in an identical manner, but without any crystallization inhibitors.

The formulation of Example 9 contained N,N-dialkyl long chain alkylamides in an amount of 30% wt. Table 9 describes the liquid formulation of Example 9 and the comparison formulation, Comparison I.

TABLE 9

| EXAMPLE 9: Diniconazole EC (with Crystallization inhibitor) | | COMPARISON I: Diniconazole EC (without Crystallization inhibitor) | | |
| --- | --- | --- | --- | --- |
| Component | Composition | Component | composition | Remark |
| Diniconazole tech | 100 kg (as pure) | Diniconazole tech | 100 kg (as part) | Active ingredient |
| Agnique ABS 60C Calcium dodecylphenyl sulphonate | 100 kg | Agnique ABS 60C Calcium dodecylphenyl sulphonate | 100 kg | Emulsifier |
| Emulsogen EL 360 Castor oil ethoxylate | 100 kg | Emulsogen EL 360 Castor oil ethoxylate | 100 kg | Emulsifier |
| Dimethyl formamide | 400 kg | Dimethyl formamide | 700 kg | Solvent |
| N,N-dipentyl-decanamide | 300 kg | | | Crystallization inhibitor |
| Total | 1000 kg | Total | 1000 kg | |

Use Example IX

The experimental results are set forth in the following table.

|  | Example 9 | | | Comparison I | | |
| --- | --- | --- | --- | --- | --- | --- |
|  | Press. (PSI) 200 mesh | Diniconazole (ppm) | Diniconazole decrease % | Press. (PSI) 200 mesh | Diniconazole (ppm) | Diniconazole decrease % |
| Initial solution | 40 | 435 | 0 | 38 | 443 | 0 |
| After 1 h | 40 | 430 | −1.15 | 38 | 346 | −21.89 |
| After 2 h | 40 | 421 | −2.07 | 39 | 270 | −39.06 |
| After 3 h | 40 | 417 | −4.14 | 40 | 184 | −58.47 |
| After 4 h | 42 | 410 | −5.75 | 40 | 107 | −75.85 |

Example 10

The formulation of Example 10 was prepared containing N,N-dialkyl long chain alkylamides, wherein the weight ratio of tebuconazole to N,N-dialkyl long chain alkylamides was approx 1:4. Crystal formation of this formulation was compared with a second liquid formulation, which was prepared from identical components in an identical manner, but without any crystallization inhibitors.

The formulation of Example 10 contained N,N-dialkyl long chain alkylamides in an amount of 40% wt. Table 10 describes the liquid formulation of Example 10 and the comparison formulation, Comparison J.

TABLE 10

| EXAMPLE 10: Tebuconazole EC (with Crystallization inhibitor) | | COMPARISON J: Tebuconazole EC (without Crystallization inhibitor) | | |
|---|---|---|---|---|
| Component | Composition | Component | Composition | Remark |
| Tebuconazole tech | 100 kg (as pure) | Tebuconazole tech | 100 kg (as pure) | Active ingredient |
| Agnique ABS 60C Calcium dodecylphenyl sulphonate | 100 kg | Agnique ABS 60C Calcium dodecylphenyl sulphonate | 100 kg | Emulsifier |
| Emulsogen EL 360 Castor oil ethoxylate | 100 kg | Emulsogen EL 360 Castor oil ethoxylate | 100 kg | Emulsifier |
| Xylene | 300 kg | Xylene | 700 kg | Solvent |
| N,N-dipentyl-octa-decanamide | 400 kg | | | Crystallization inhibitor |
| Total | 1000 kg | Total | 1000 kg | |

Use Example X

The experimental results are set forth in the following table.

| | Example 10 | | | Comparison J | | |
|---|---|---|---|---|---|---|
| | Pressure (PSI) 200 mesh | Tebuconazole (ppm) | Tebuconazole decrease % | Pressure (PSI) 200 mesh | Tebuconazole (ppm) | Tebuconazole decrease % |
| Initial solution | 40 | 438 | 0 | 38 | 447 | 0 |
| After 1 h | 40 | 430 | −1.83 | 38 | 300 | −32.89 |
| After 2 h | 40 | 414 | −5.48 | 41 | 143 | −68.00 |
| After 3 h | 39 | 408 | −6.85 | Nozzles 100% blocked | | |
| After 4 h | 42 | 400 | −8.68 | Nozzles 100% blocked | | |

Example 11

The formulation of Example 11 was prepared containing N,N-dialkyl long chain alkylamides, wherein the weight ratio of tricyclazole to N,N-dialkyl long chain alkylamides was approx 1:2.2. Crystal formation of this formulation was compared with a second liquid formulation, which was prepared from identical components in an identical manner, but without any crystallization inhibitors.

The formulation of Example 11 contained N,N-dialkyl long chain alkylamides in an amount of 55% wt. Table 11 describes the liquid formulation of Example 11 and the comparison formulation, Comparison K.

TABLE 11

| EXAMPLE 11: Tricyclazole EC (Containing Crystallization inhibitors) | | COMPARISON K: Tricyclazole EC (Not containing Crystallization inhibitors) | | |
|---|---|---|---|---|
| Component | Composition | Component | Composition | Remark |
| Tricyclazole tech | 250 kg (as pure) | Tricyclazole tech | 250 kg (as pure) | Active ingredient |
| Agnique ABS 70 C Calcium dodecylphenyl sulphonate | 80 kg | Agnique ABS 70 C Calcium dodecylphenyl sulphonate | 80 kg | Emulsifier |
| Emulsogen EL 360 Castor oil ethoxylate | 120 kg | Emulsogen EL 360 Castor oil ethoxylate | 120 kg | Emulsifier |
| Dimethyl formamide | | Dimethyl formamide | 550 kg | Solvent |
| N,N-dipropyl-dodecanamide | 350 kg | | | Crystallization inhibitor |
| N,N-dibutyl-decanamide | 200 kg | | | Crystallization inhibitor |
| Total | 1000 kg | Total | 1000 kg | |

Use Example XI

The experimental results are set forth in the following table.

| | Example 11 | | | Comparison K | | |
|---|---|---|---|---|---|---|
| | Pressure (PSI) 200 mesh | Tricyclazole (ppm) | Tricyclazole decrease % | Pressure (PSI) 200 mesh | Tricyclazole (ppm) | Tricyclazole decrease % |
| Initial solution | 40 | 1250 | 0 | 40 | 1262 | 0 |
| After 1 h | 40 | 1197 | −4.24 | 40 | 863 | −31.62 |
| After 2 h | 40 | 1138 | −8.96 | 41 | 654 | −48.18 |
| After 3 h | 39 | 1106 | −11.52 | Nozzles 100% blocked | | |
| After 4 h | 42 | 1097 | −12.24 | Nozzles 100% blocked | | |

Example 12

The formulation of Example 12 was prepared containing flutriafol as the active ingredient and N,N-dialkyl long chain alkylamides, wherein the weight ratio of flutriafol to N,N-dialkyl long chain alkylamides was approx 1:1.6. Crystal formation of this formulation was compared with a second liquid formulation, which was prepared from identical components in an identical manner, but without any crystallization inhibitors.

The formulation of Example 12 contained N,N-dialkyl long chain alkylamides in an amount of 40% wt. Table 12 describes the liquid formulation of Example 12 and the comparison formulation, Comparison L.

TABLE 12

| EXAMPLE 12: Flutriafol EC (Containing Crystallization inhibitors) | | COMPARISON L: Flutriafol EC (Not containing Crystallization inhibitors) | | |
|---|---|---|---|---|
| Component | Composition | Component | Composition | Remark |
| Flutriafol tech | 250 kg (as pure) | Flutriafol tech | 250 kg (as pure) | Active ingredient |
| Agnique ABS 70 C Calcium dodecylphenyl sulphonate | 80 kg | Agnique ABS 70 C Calcium dodecylphenyl sulphonate | 80 kg | Emulisifier |
| Emulsogen EL 360 Castor oil ethoxylate | 100 kg | Emulsogen EL 360 Castor oil ethoxylate | 100 kg | Emulisifier |

TABLE 12-continued

| EXAMPLE 12: Flutriafol EC (Containing Crystallization inhibitors) | | COMPARISON L: Flutriafol EC (Not containing Crystallization inhibitors) | | |
|---|---|---|---|---|
| Component | Composition | Component | Composition | Remark |
| Dimethyl formamide | 170 kg | Dimethyl formamide | 570 kg | Solvent |
| N,N-dipropyl-dodecanamide | 300 kg | | | Crystallization inhibitor |
| N,N-dipentyl-octanamide | 100 kg | | | Crystallization inhibitor |
| Total | 1000 kg | Total | 1000 kg | |

Use Example XII

The experimental results are set forth in the following table.

| | Example 12 | | | Comparison L | | |
|---|---|---|---|---|---|---|
| | Pressure (PSI) 200 mesh | Flutriafol (ppm) | Flutriafol decrease % | Pressure (PSI) 200 mesh | Flutriafol (ppm) | Flutriafol decrease % |
| Initial solution | 40 | 1133 | 0 | 40 | 1253 | 0 |
| After 1 h | 40 | 1106 | −2.38 | 42 | 690 | −44.96 |
| After 2 h | 40 | 1059 | −8.96 | Nozzles 100% blocked | | |
| After 3 h | 39 | 1022 | −9.79 | Nozzles 100% blocked | | |
| After 4 h | 42 | 998 | −11.92 | | | |

Example 13

The formulation of Example 13 was prepared containing N,N-dialkyl long chain alkylamides, wherein the weight ratio of tebuconazole to N,N-dialkyl long chain alkylamides was approx 1:1.2. Crystal formation of this formulation was compared with a second liquid formulation, which was prepared from identical components in an identical manner, but containing an alkylamide with a lower alkyl constituent group.

The formulation of Example 13 contained N,N-dialkyl long chain alkylamides in an amount of 30% wt. Table 13 describes the liquid formulation of Example 13 and the comparison formulation, Comparison M, in which the lower alkyl alkylamide was used.

TABLE 13

| EXAMPLE 13: Tebuconazole EC (with long chain alkylamide) | | COMPARISON M: Tebuconazole EC (with lower chain alkylamide) | | |
| --- | --- | --- | --- | --- |
| Component | Composition | Component | Composition | Remark |
| Tebuconazole tech | 250 kg (as pure) | Tebuconazole tech | 250 kg (as pure) | Active ingredient |
| Agnique ABS 60C Calcium dodecylphenyl sulphonate | 100 kg | Agnique ABS 60C Calcium dodecylphenyl sulphonate | 100 kg | Emulsifier |
| Emulsogen EL 360 Castor oil ethoxylate | 100 kg | Emulsogen EL 360 Castor oil ethoxylate | 100 kg | Emulsifier |
| Xylene | 250 kg | Xylene | 250 kg | Solvent |
| N,N-diethyl-dodecanamide | 300 kg | N,N-diethyl-octanamide | 300 kg | Crystallization inhibitor |
| Total | 1000 kg | Total | 1000 kg | |

Use Example XIII

The experimental results are set forth in the following table.

| | Example 13 | | | Comparison M | | |
| --- | --- | --- | --- | --- | --- | --- |
| | Press. (PSI) 200 mesh | Tebuconazole (ppm) | Tebuconazole decrease % | Press. (PSI) 200 mesh | Tebuconazole (ppm) | Tebuconazole decrease % |
| Initial solution | 40 | 1133 | 0 | 40 | 1253 | 0 |
| After 1 h | 40 | 1106 | −2.38 | 40 | 1054 | −15.88 |
| After 2 h | 40 | 1059 | −8.96 | 41 | 906 | −27.66 |
| After 3 h | 39 | 1022 | −9.79 | 41 | 579.4 | −53.76 |
| After 4 h | 42 | 998 | −11.92 | 40 | 504.3 | −59.75 |

Example 14

The formulation of Example 14 was prepared containing N,N-dialkyl long chain alkylamides, wherein the weight ratio of tebuconazole to N,N-dialkyl long chain alkylamides was approx 1:1.2. Crystal formation of this formulation was compared with a second liquid formulation, which was prepared from identical components in an identical manner, but containing an alkylamide with lower alkyl constituent groups.

The formulation of Example 14 contained N,N-dialkyl long chain alkylamides in an amount of 30% wt. Table 14 describes the liquid formulation of Example 14 and the comparison formulation, Comparison N.

TABLE 14

| EXAMPLE 14: Tebuconazole EC (with long chain alkylamide) | | COMPARISON N: Tebuconazole EC (with lower chain alkylamide) | | |
| --- | --- | --- | --- | --- |
| Component | Composition | Component | Composition | Remark |
| Tebuconazole tech | 250 kg (as pure) | Tebuconazole tech | 250 kg (as pure) | Active ingredient |
| Agnique ABS 60C Calcium dodecylphenyl sulphonate | 100 kg | Agnique ABS 60C Calcium dodecylphenyl sulphonate | 100 kg | Emulsifier |
| Emulsogen EL 360 Castor oil ethoxylate | 100 kg | Emulsogen EL 360 Castor oil ethoxylate | 100 kg | Emulsifier |
| Xylene | 250 kg | Xylene | 250 kg | Solvent |
| N,N-dipropyl-dodecanamide | 300 kg | N,N-dipropyl-nonamide | 300 kg | Crystallization inhibitor |
| Total | 1000 kg | Total | 1000 kg | |

Use Example XIV

The experimental results are set forth in the following table.

|  | Example 14 | | | Comparison N | | |
| --- | --- | --- | --- | --- | --- | --- |
|  | Press. (PSI) 200 mesh | Tebuconazole (ppm) | Tebuconazole decrease % | Press. (PSI) 200 mesh | Tebuconazole (ppm) | Tebuconazole decrease % |
| Initial solution | 40 | 1098 | 0 | 40 | 1148 | 0 |
| After 1 h | 40 | 1057 | −3.73 | 40 | 712 | −37.98 |
| After 2 h | 40 | 1044 | −4.92 | 42 | 564 | −50.87 |
| After 3 h | 39 | 1026 | −6.56 | 46 | 484 | −57.88 |
| After 4 h | 42 | 994 | −9.47 | 46 | 402 | −65.03 |

Example 15

The formulation of Example 15 was prepared containing N,N-dialkyl long chain alkylamides, wherein the weight ratio of tebuconazole to N,N-dialkyl long chain alkylamides was approx 1:1.2. Crystal formation of this formulation was compared with a second liquid formulation, which was prepared from identical components in an identical manner, but containing an alkylamide with lower alkyl groups.

The formulation of Example 15 contained N,N-dialkyl long chain alkylamides in an amount of 30% wt. Table 15 describes the liquid formulation of Example 15 and the comparison formulation, Comparison O

| EXAMPLE 15: Tebuconazole EC (with long chain alkylamide) | | COMPARISON O: Tebuconazole EC (with lower chain alkylamide) | | |
| --- | --- | --- | --- | --- |
| Component | Composition | Component | Composition | Remark |
| Tebuconazole tech | 250 kg (as pure) | Tebuconazole tech | 250 kg (as pure) | Active ingredient |
| Agnique ABS 60C | 100 kg | Agnique ABS 60C | 100 kg | Emulsifier |
| Calcium dodecylphenyl sulphonate |  | Calcium dodecylphenyl sulphonate |  |  |
| Emulsogen EL 360 | 100 kg | Emulsogen EL 360 | 100 kg | Emulsifier |
| Castor oil ethoxylate |  | Castor oil ethoxylate |  |  |
| Xylene | 250 kg | Xylene | 250 kg | Solvent |
| N,N-dibutyl-octanamide | 300 kg | N,N-dibutyl-hexamide | 300 kg | Crystallization inhibitor |
| Total | 1000 kg | Total | 1000 kg |  |

Use Example No. XV

The experimental results of the test for crystal formation are set out in the table which follows.

|  | Example 15 | | | Comparison O | | |
| --- | --- | --- | --- | --- | --- | --- |
|  | Press. (PSI) 200 mesh | Tebuconazole (ppm) | Tebuconazole decrease % | Press. (PSI) 200 mesh | Tebuconazole (ppm) | Tebuconazole decrease % |
| Initial solution | 40 | 1243 | 0 | 40 | 1234 | 0 |
| After 1 h | 40 | 1195 | −3.86 | 40 | 743 | −39.79 |
| After 2 h | 40 | 1154 | −7.16 | Nozzles 100% blocked |  |  |
| After 3 h | 39 | 1138 | −8.45 | Nozzles 100% blocked |  |  |
| After 4 h | 41 | 1102 | −11.3 |  |  |  |

From the experimental data set out above, it can be seen that the long chain alkyl amides of Formula I above exhibit significant performance in inhibiting the crystallization of the pesticidally active azole derivatives. In particular, the long chain alkyl amides perform significantly better than the corresponding lower alkyl compounds and exhibit a markedly higher activity in preventing crystallization of the azole derivatives.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art form the foregoing description and fall within the scope of the appended claims. The advantages and objects of the invention are not necessarily encompassed by each embodiment of the invention.

The invention claimed is:

1. An agrochemical composition comprising an N,N-dialkyl long chain alkylamide of the formula (I)

in which:
R$^1$ and R$^2$ are each independently normal alkyl radicals having from 2 to 20 carbon atoms and R represents an alkyl group having from 6 to 30 carbon atoms;
wherein the total number of carbon atoms in R, R$^1$ and R$^2$ is greater than 18;
and at least one azole active ingredient;
and optionally at least one member selected from the group consisting of a surface-active agent, organic diluent and low temperature stabilizer.

2. The composition according to claim 1, wherein R represents an alkyl group having from 6 to 25 carbon atoms.

3. The composition according to claim 1, wherein R$^1$ and R$^2$ each represent an alkyl group having from 4 to 12 carbon atoms.

4. The composition according to claim 1, wherein R is a normal alkyl group.

5. The composition according to claim 1, wherein the ratio of azole active ingredient and N,N-dialkyl long chain alkylamide is from 1:0.1 to 1:5.

6. The composition according to claim 1, wherein two or more N,N-dialkyl long chain alkylamides are present.

7. The composition according to claim 1, wherein two or more azole active ingredients are present.

8. The composition according to claim 1, wherein the N,N-dialkyl long chain alkylamide is selected from the group consisting of N,N-diethylhexadecanamide, N,N-diethylheptadecanamide, N,N-diethyloctadecanamide, N,N-diethylnonadecanamide, N,N-dipropyltetradecanamide, N,N-diethylhexadecanamide, N,N-dipropylheptadecanamide, N,N-dipropyl octadecanamide, N,N-dipropylnonadecanamide, N,N-dibutyldodecanamide, N,N-dibutyltridecanamide, N,N-dibutyltetradecanamide, N,N-dibutylhexadecanamide, N,N-dibutylheptadecanamide, N,N-dibutyloctadecanamide, N,N-dibutylnonadecanamide, N,N-dipentyloctanamide, N,N-dipentyldecanamide, N,N-dipentyldodecanamide, N,N-dipentyltetradecanamide, N,N-dipentylhexadecanamide, N,N-dipentyloctadecanamide, or any mixture thereof.

9. The composition according to claim 1, wherein the N,N-dialkyl long chain alkylamide is present in an amount of from 5% to 80% by weight.

10. The composition according to claim 1, wherein the azole active ingredient is selected from tebuconazole, cyproconazole, triticonazole, hexaconazole, flutriafol, myclobutanil and mixtures thereof.

11. The composition according to claim 1, wherein the azole active ingredient is selected from difenoconazole, diniconazole, propiconazole, tricyclazole, triticonazole, triflumizole, flusilazole, metconazole.

12. The composition according to claim 1, further comprising a solvent or diluent.

13. The composition according to claim 12, wherein the solvent or diluent is dimethyl formamide or xylene.

14. The composition according to claim 1, further comprising an emulsifier.

15. An aqueous spray composition comprising a composition according to claim 1 and water.

16. The composition according to claim 15, wherein the azole active ingredient is present in an amount of from 0.0001% to 3% by weight.

17. A method of preventing crystallization of pesticidal liquid formulations comprising azole active ingredient as defined in claim 1 during application, the method comprising adding a N,N-dialkyl long chain alkylamide as defined in claim 1 to the formulation in an amount sufficient to reduce crystallization of the azole active ingredient.

18. A method of treating pests at a locus comprising applying to the locus a composition according to claim 1.

19. The method according to claim 18, wherein the composition is applied in the form of a diluted aqueous formulation.

20. The method according to claim 17, wherein the composition comprises a fungicidally active compound and treats fungal infestations of plants in the locus.

21. The method according to claim 18, wherein the composition comprises a fungicidally active compound and treats fungal infestations of plants in the locus.

22. The composition according to claim 1, wherein R represents an alkyl group having from 6 to 18 carbon atoms.

23. The composition according to claim 1, wherein R$^1$ and R$^2$ each represent an alkyl group having from 4 to 8 carbon atoms.

24. The composition according to claim 1, wherein the total number of carbon atoms in R, R$^1$ and R$^2$ is greater than 20.

25. The composition according to claim 1, wherein the ratio of azole active ingredient and N,N-dialkyl long chain alkylamide is from 1:1 to 1:4.

26. The composition according to claim 1, wherein the N,N-dialkyl long chain alkylamide is present in an amount of from 20% to 60% by weight.

27. The composition according to claim 15, wherein the azole active ingredient is present in an amount of from 0.002% to 2% by weight.

* * * * *

UNITED STATES PATENT AND TRADEMARK OFFICE
CERTIFICATE OF CORRECTION

PATENT NO. : 8,653,121 B2  Page 1 of 1
APPLICATION NO. : 12/602066
DATED : February 18, 2014
INVENTOR(S) : Yin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 812 days.

Signed and Sealed this

Twenty-ninth Day of September, 2015

Michelle K. Lee
*Director of the United States Patent and Trademark Office*